United States Patent [19]

Larkin

[11] 4,137,254

[45] Jan. 30, 1979

[54] PREPARATION OF AROMATIC NITRILES

[75] Inventor: John M. Larkin, Austin, Tex.

[73] Assignee: Texaco, Inc., New York, N.Y.

[21] Appl. No.: 819,512

[22] Filed: Jul. 27, 1977

[51] Int. Cl.$^2$ .................. C07C 120/14; C07C 121/78
[52] U.S. Cl. .............................. 260/465 E; 260/465 C; 260/580
[58] Field of Search ................ 260/465 C, 465 E, 580

[56] References Cited

U.S. PATENT DOCUMENTS

| 3,079,422 | 2/1963 | Pasky ................................ 260/465 C |
| 3,136,818 | 6/1964 | Sperber et al. ....................... 260/580 |
| 3,231,600 | 1/1966 | Jones et al. ....................... 260/465 C |
| 3,783,142 | 1/1974 | Bakke et al. ....................... 260/465 E |
| 3,803,204 | 4/1974 | Grasselli et al. ................. 260/465 C |

Primary Examiner—Dolph H. Torrence
Attorney, Agent, or Firm—Thomas H. Whaley; Carl G. Ries; George J. Darsa

[57] ABSTRACT

Aromatic nitriles are prepared from methylated aromatic hydrocarbons, such as toluene, xylene, tri- and tetramethylbenzenes by contacting at an elevated temperature with a nitroaromatic compound and ammonia in the presence of a catalyst composed of two or more metal oxides of the metals of Groups I B, III B, V A, VI B, VII B and VIII of the Periodic Table. A valuable coproduct of the method is an aromatic amine.

28 Claims, No Drawings

PREPARATION OF AROMATIC NITRILES

BACKGROUND OF THE INVENTION

This invention relates to a novel method of preparing aromatic nitriles. In particular, this invention relates to a method of preparing aromatic nitriles by the catalytic ammoxidation of methylated aromatic hydrocarbons.

Aromatic nitriles represent a class of important compounds, the most well-known of which is benzonitrile. Aromatic nitriles, for example benzonitrile, can be prepared by distilling ammonium benzoate or by the condensation of benzenediazonium chloride with potassium cyanide. Another method for producing aromatic nitriles is described in U.S. Pat. No. 3,433,821 which comprises reacting an aromatic compound, such as benzene, and a cyanogen halide, e.g., cyanogen chloride, in the presence of an aluminosilicate catalyst. U.S. Pat. No. 3,783,142 describes the preparation of o-aminobenzonitrile from o-nitrotoluene and ammonia employing as catalyst silica gel, alumina or a synthetic zeolite. Aromatic nitriles can also be prepared by distilling the mixture of a salt of an aromatic sulfonic acid and potassium cyanide or by the Friedel-Crafts-Karrer synthesis wherein aromatic hydrocarbons are condensed with cyanogen chloride in the presence of aluminum chloride. Commercially, aromatic nitriles, such as benzonitrile are utilized in the manufacture of resins and plastics and are also used as solvents for a variety of elastomer materials.

It is an object of this invention to provide a novel method for preparing aromatic nitriles.

It is another object of this invention to provide a catalytic method for the preparation of aromatic nitriles.

Yet another object of this invention is to provide a method for preparing aromatic nitriles from methylated aromatic hydrocarbons.

Other objects and advantages will become apparent from a reading of the following detailed description and examples.

SUMMARY OF THE INVENTION

Broadly, this invention contemplates a method for preparing aromatic nitriles which comprises contacting a methylated aromatic compound with ammonia and a nitroaromatic compound in the presence of a catalyst comprising two or more oxides of the metals of Groups I B, III B, V A, VI B, VII B and VIII of the Periodic Table.

According to this invention, the aromatic nitriles are prepared from methylated aromatic hydrocarbons, suitably methylbenzenes having from 1 to 4 methyl groups. Illustrative of the methylated aromatic hydrocarbons are toluene, o-xylene, m-xylene, p-xylene, hemimellitine (1,2,3-trimethylbenzene), pseudocumene (1,2,4-trimethylbenzene), mesitylene (1,3,5-trimethylbenzene), prehnitine (1,2,3,4-tetramethylbenzene), isodurene (1,2,3,5-tetramethylbenzene), and durene (1,2,4,5-tetramethylbenzene). Individual or mixtures of methylbenzenes, such as toluene and one or more xylenes or o-, m-, and p-xylene, or pseudocumene and durene can be employed.

The nitroaromatic compounds utilized in accordance with the method of this invention includes nitrobenzene and dinitrobenzene, such as 1,2-dinitrobenzene, 1,3-dinitrobenzene and 1,4-dinitrobenzene. Individual or mixtures of nitrobenzenes can be employed and the nitroaromatic of choice is nitrobenzene.

In a particularly preferred embodiment, the methylated aromatic hydrocarbon additionally contains a nitro group. In this instance, the requirement in the method for a methylated aromatic and a nitroaromatic can be satisfied through the use of a single compound. For example, the methylated and nitroaromatic compound can be o-nitrotoluene, m-nitrotoluene, p-nitrotoluene, 2-nitro-m-xylene, 4-nitro-o-xylene, 2-nitro-p-xylene, a nitrotrimethylbenzene or a nitrotetramethylbenzene. Individual or mixtures of methylated nitroaromatics can be utilized, such as mixtures of nitrotoluenes or nitroxylenes or nitrotoluenes and nitroxylenes. It will be appreciated that a methylated aromatic hydrocarbon can also be present, if desired, in addition to the methylated nitroaromatic.

Pursuant to the method of this invention, the methylated aromatic compound and nitroaromatic compound or nitromethylaromatic compound alone or in the presence of a methylated aromatic compound are contacted with ammonia at an elevated temperature and the metal oxide catalyst. The contacting of the reactants can be conducted, if desired, in the presence of an inert organic diluent, such as benzene, cyclohexane, naphthalene, heptane, methylcyclopentane, hexane, biphenyl or dodecane. In general, the diluents can be saturated hydrocarbons or aromatic hydrocarbons having a boiling point of about 20 to 260° C. The aromatic hydrocarbons, other than the reactants, preferably do not bear alkyl substituents on the aromatic ring.

In the course of the reaction and under the conditions described herein, a nitrile is formed from the aromatic compound's methyl group and additionally the aromatic's nitro group is converted to an amino group. Illustratively, the contacting of nitrobenzene and toluene produces benzonitrile and as a valuable coproduct, aniline. In those instances where a methylated nitroaromatic is employed, such as o-nitrotoluene, an amino-substituted aromatic nitrile is produced, such as o-aminobenzonitrile, along with aminotoluene.

In the reaction described above, the presence of ammonia is necessary to insure the formation of the aromatic nitrile. In the absence of ammonia, nitriles do not form. Instead the resulting product is an aromatic amine or a Schiff base. The amount of ammonia needed to insure nitrile formation from the methylated aromatic compound generally ranges from about 1:0.03 and 1:1 moles of methylated aromatic compound per mole of ammonia. Likewise, the moles of methylated aromatic to nitroaromatic compound is generally about 1:1, but suitable ratios of from 1:0.1 to 1:10 can also be employed.

The catalysts employed in the present method comprise two or more metal oxides of the metals of Groups I B, III B, V A, VI B, VII B and VIII of the Periodic Table. Preferred metal oxides are of the metals copper, antimony, molybdenum, chromium, uranium, cobalt, nickel and iron. More particularly, combinations of metal oxides of Group V A and III B, VII B or VIII, or combinations of metal oxides of Group VI B and I B or VIII are preferred. Highly preferred combinations of metal oxides employed as the catalyst in the instant method include the oxides of the metals antimony and iron, antimony and uranium, copper and chromium, nickel and molybdenum and cobalt and molybdenum. The most highly preferred catalysts are composed of the oxides of antimony and iron or antimony and uranium or copper and chromium. The aforementioned metal oxides can be combined with the support wherein the support comprises from about 10 to 90 weight percent of the catalyst. Typical supports include silica, alumina, zirconia, borates, carbonates, silicon carbide, carbon, charcoal and mixtures of silica and alumina. The catalysts employed in the instant method, in general, represent commercially available materials, particularly, such metal oxide catalysts as copper chromite; nickel oxide, molybdenum oxide on a support of alumina; cobalt oxide, molybdenum oxide on a support of silica and cobalt and chromium oxides on a support of alumina. The preferred metal oxide catalysts are those of antimony and iron or antimony and uranium and the same are respectively described in, for example, U.S. Pat. Nos. 3,197,419 and 3,198,750.

The method described herein wherein a methylated aromatic compound is contacted with ammonia and nitroaromatic in the presence of the aforementioned catalyst is conveniently undertaken at temperatures of from about 419 to 950° F. (215–510° C.) and preferably from about 750 to 900° F. (399–483° C.) at pressures of from about 0.9 to 10 atmospheres. Reaction temperatures below 215° C. are generally insufficient to enable the catalytic reaction to proceed and temperatures exceeding 510° C. degrade the reactants and convert the same to carbon dioxide and water.

The method can be conducted batchwise or in a continuous manner. Suitable reactors may be charged with catalyst and the methylated aromatic and nitroaromatic introduced thereto along with ammonia. Alternately, the methylated- and nitrated aromatic materials along with ammonia can be passed through a bed of catalyst at a liquid hourly space velocity of about 0.1 to 5. If desired, an inert diluent can be used in the batch or continuous process.

Typical aromatic nitriles prepared according to this method include benzonitrile, o-toluonitrile m-toluonitrile, p-toluonitrile, dimethylbenzonitrile, o-aminobenzonitrile, m-aminobenzonitrile, p-aminobenzonitrile, methylaminobenzonitrile, 1-cyanonaphthalene, 2-cyanonaphthalene, 1-amino-2-cyanonaphthalene and 2-amino-4-cyanonaphthalene. Typical aromatic amines formed as coproducts include aniline, o-toluidine, p-toluidine, m-toluidine, 1-aminonaphthalene and 2-aminonaphthalene.

The aromatic nitrile can be recovered at the completion of the reaction by, for example, dissolving the crude reaction product in a suitable solvent such as ethylether, benzene, cyclohexane, or chlorobenzene followed by extraction with a dilute solution of hydrochloric acid to remove the aromatic amine. The amine is sprung from the acid extract using a dilute sodium hydroxide solution. The sprung amine can be taken up and separated from the alkali solution using a solvent such as ether, benzene or cyclohexane. Thereafter the solvent can be removed by distillation and the aromatic amine recovered.

The organic raffinate of the crude product composed of solvent and aromatic nitrile is stripped to remove the solvent. The aromatic nitrile residue can be further purified by distillation.

In order to more fully illustrate the nature of this invention and the manner of practicing the same, the following examples are presented.

EXAMPLE 1

An antimony oxide-iron oxide catalyst was prepared according to Example 1 of U.S. Pat. No. 3,197,419 in the form of 5/32 inch diameter tablets. 75 grams of the catalyst was placed in a one-inch upright tubular reactor and the catalyst bed measured three inches in height. The reactor was heated to 750° F. and dry nitrogen was introduced at the rate of 100 cc per minute for one hour and thereafter gaseous ammonium at 96 cc per minute for 15 minutes. While maintaining the rate of ammonia introduction, 12.0 grams of p-nitrotoluene and 14.0 grams of benzene were simultaneously charged to the reactor over a period of about 3 hours. The product from the first 40 minutes of the run was discarded. The product subsequently collected weighed 16.7 grams and consisted of two layers. The upper red-brown liquid layer (11.50 grams) was by gas-liquid chromatography identified as (on a benzene-free basis) 5% unconverted p-nitrotoluene, 47.5% p-aminobenzonitrile and 47.5% p-toluidine.

The diluent benzene is removed by distillation at atmospheric pressure and the products separated by distillation at 5.5 mm. Hg. The p-toluidine distills as a pure cut followed by p-nitrotoluene. The residue consists of p-aminobenzonitrile which solidifies when cooled to room temperature.

EXAMPLE 2

An antimony oxide-uranium oxide on silica catalyst was prepared according to Example 11 of U.S. Pat. No. 3,198,750 in the form of 5/32 inch diameter tablets and calcined at 800° F. for four hours. 67 grams of the catalyst was placed in the reactor as in Example 1 and the catalyst bed measured four and one-half inches in height. Ammonia, p-nitrotoluene and benzene were charged to the reactor as in Example 1 and 11.82 grams of an upper red-brown liquid was collected and identified by gas-liquid chromatography to be on a benzene-free basis 51% unconverted p-nitrotoluene, 28% p-aminobenzonitrile and 23% p-toluidine.

EXAMPLE 3

Fifty grams of a commercially available nickel and molybdenum oxides (3% NiO, 15% $MoO_3$) on an alumina support catalyst was placed in the reactor of Example 1 and had a bed height of 5.5 inches. A solution of 4.34 grams of nitrobenzene and 12.00 grams of toluene was charged continuously together with 96 cc per minute of ammonia over a period of about 2 hours. The product from the first 40 minutes of the run was discarded. The product subsequently collected weighed 8.23 grams of which 6.06 grams was a cloudy yellow top phase. The top phase was combined with 40 milliliters of 1.2 N aqueous HCl and the mixture was extracted with two 25 milliliter portions of ethylether. The ethereal extract was dried over anhydrous magnesium sulfate and filtered. After stripping the filtrate at 30° C. and 25 mm. Hg., 0.24 gram of an amber liquid was recovered and identified by infra-red analysis to be benzonitrile. The aqueous portion of the extraction was made alkaline by adding 10% aqueous NaOH and the resulting solution was extracted with ethylether. This ethereal extract was dried, filtered and stripped as above, and 0.96 gram of an amber liquid was recovered and identified by infra-red to be aniline.

EXAMPLE 4

The procedure of Example 1 was repeated except that the catalyst consisted of cobalt, molybdenum and boron oxides. The catalyst was prepared by dissolving 100 grams of boric acid in a solution of 144 grams of $MoO_3$, 300 cc of concentrated aqueous ammonium hydroxide and sufficient water to make four liters of solution. This solution was heated to 200° F. and mixed with 292 grams of cobalt nitrate in 400 cc of water. The precipitate formed was filtered, dried at 300° F. for 16 hours and calcined at 750° F. for 4 hours. 132 grams of catalyst was employed. Following the procedure of Example 1, the product was recovered and analyzed by gas-liquid chromatography to be on a benzene-free basis 17% p-aminobenzonitrile and 83% p-toluidine. No p-nitrotoluene remained unconverted.

EXAMPLE 5

Example 1 was repeated except that the feed solution consisted of 5.0 grams of p-nitrotoluene and 17.0 grams of cyclohexane charged to the reactor at 0.193 cc per minute along with an ammonia rate of 60 cc per minute. The catalyst employed was a commercially available copper chromite (42% Cu, 26% Cr) in the form of 3/16" × ⅛" tablets and the reaction temperature was maintained at about 658–673° F. Gas-liquid chromatography identified the product on a cyclohexane free basis as 58.7% p-toluidine, 5.5% p-aminobenzonitrile and 35.8% unconverted p-nitrotoluene.

EXAMPLE 6

The procedure of Example 5 was repeated except that o-nitrotoluene was substituted for p-nitrotoluene, 10.0 grams of cyclohexane was used, the liquid charge rate was 0.150 milliliters per minute, the ammonia rate was 70 cc per minute and the reactor temperature 845–861° F. Analysis of the product as in Example 5 indicated 11.1% o-aminobenzonitrile, 43.8% o-toluidine, 0.4% unconverted starting material and the remainder unidentified compounds.

Example 7

The procedure of Example 5 was repeated except that the feed consisted of 4.34 grams of nitrobenzene and 12.0 grams of toluene charged at 0.171 milliliters per minute, an ammonia flow rate of 84 cc per minute and a reactor temperature of 851–860° F. Analysis of the product indicates 7% benzonitrile and 75% aniline.

By contrast, when nitrogen was substituted for ammonia under essentially the same conditions, the product consisted of 46% aniline, 36% unconverted nitrobenzene and 7.2% of the anil of benzaldehyde.

EXAMPLE 8

The procedure of Example 5 was repeated except that the feed consisted of 8.75 grams of 1,3-dimethyl-2-nitrobenzene and 17.5 grams of cyclohexane charged at 0.147 milliliters per minute and a reactor temperature of 820–831° F. The product was identified as containing 10.1% 2-amino-3-methylbenzonitrile, 28.6% 2,6-dimethylaniline and 12% unconverted material.

EXAMPLE 9

A mixture of 6.85 grams of p-nitrotoluene, 50 grams of naphthalene and 4.0 grams of copper chromite was stirred at 212–126° C. for 16 hours while ammonia was introduced at 43–70 cc per minute. After cooling, diluting with 200 milliliters of diethylether and filtering, the filtrate was extracted with 95 milliliters of 1.2 N aqueous HCl. The aqueous layer was made basic with a 10% NaOH solution and extracted twice with 60 milliliter portions of ether. The ether extract was dried over anhydrous magnesium sulfate, stripped at about 30° C. and 30 mm. Hg. and a red-brown oil was recovered and identified by gas liquid chromatography and infra-red analyses to be 98.4% p-aminobenzonitrile and 1.6% p-toluidine.

I claim:

1. A method for preparing an aromatic nitrile which comprises contacting a methylated aromatic hydrocarbon having 1 to 4 methyl groups with ammonia and a nitroaromatic hydrocarbon having 1 to 2 nitro-groups in the presence of an ammoxidation catalyst comprising two or more oxides of the metals of Groups I B, III B, V A, VI B, VII B, and VIII of the Periodic Table at a temperature of from about 419 to 950° F.

2. A method according to claim 1 wherein said methylaromatic is toluene.

3. A method according to claim 1 wherein said methylaromatic is xylene.

4. A method according to claim 1 wherein said methylaromatic is a trimethylbenzene.

5. A method according to claim 1 wherein said methylaromatic is a tetramethylbenzene.

6. A method according to claim 1 wherein said nitroaromatic compound is nitrobenzene.

7. A method according to claim 1 wherein said nitroaromatic compound is a dinitrobenzene.

8. A method according to claim 1 wherein said methylated aromatic hydrocarbon is a methylbenzene having from 1 to 4 methyl groups.

9. A method according to claim 8 wherein said methylated aromatic hydrocarbon contains a nitro group.

10. A method according to claim 8 wherein said methylated aromatic hydrocarbon is nitrotoluene.

11. A method according to claim 8 wherein said methylated aromatic hydrocarbon is a nitroxylene.

12. A method according to claim 1 wherein the mole ratio of methylated aromatic compound to ammonia is from about 1:0.03 to about 1:1.

13. A method according to claim 1 wherein said contacting is undertaken at a temperature of from about 215 to 510° C.

14. A method according to claim 1 wherein said catalyst comprises two or more oxides of the metals copper, uranium, antimony, molybdenum, chromium, cobalt, nickel or iron.

15. A method according to claim 1 wherein said catalyst comprises oxides of antimony and iron.

16. A method according to claim 1 wherein said catalyst comprises the oxides of antimony and uranium.

17. A method according to claim 1 wherein said catalyst comprises the oxides of copper and chromium.

18. A method according to claim 1 wherein said catalyst comprises the oxides of nickel and molybdenum.

19. A method according to claim 1 wherein said catalyst comprises the oxides of cobalt and molybdenum.

20. A method according to claim 1 wherein an aromatic amine is formed from said nitroaromatic hydrocarbon as a coproduct.

21. A method according to claim 20 wherein said aromatic amine is aniline.

22. A method according to claim 20 wherein said aromatic amine is p-toluidine.

23. A method according to claim 20 wherein said aromatic amine is o-toluidine.

24. A method according to claim 20 wherein said aromatic amine is 2,6-dimethylaniline.

25. A method according to claim 1 wherein said methylated aromatic compound and said nitroaromatic compound are each a methylated nitrobenzene having from 1 to 4 methyl groups.

26. A method according to claim 25 wherein said methylated nitrobenzene is p-nitrotoluene.

27. A method according to claim 25 wherein said methylated nitrobenzene is o-nitrotoluene.

28. A method according to claim 25 wherein said methylated nitrobenzene is 1,3-dimethyl-2-nitrobenzene.

* * * * *